United States Patent
Kim et al.

(10) Patent No.: US 11,844,942 B2
(45) Date of Patent: Dec. 19, 2023

(54) METHOD OF INHIBITING PROLIFERATION OF TUMOR CELL USING TRIBOELECTRIC ENERGY GENERATOR USING ULTRASONIC WAVE

(71) Applicant: Research & Business Foundation Sungkyunkwan University, Suwon-si (KR)

(72) Inventors: SangWoo Kim, Yongin-si (KR); Hong Joon Yoon, Goyang-si (KR); Dong Min Lee, Suwon-si (KR); Young Jun Kim, Daejeon (KR); Ji Hye Kim, Suwon-si (KR); Bo Sung Kim, Suwon-si (KR); Jae Hwan Jung, Suwon-si (KR); Dong Hyeon Kang, Suwon-si (KR); Tae Hyeong Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 409 days.

(21) Appl. No.: 17/104,546

(22) Filed: Nov. 25, 2020

(65) Prior Publication Data
US 2021/0170169 A1    Jun. 10, 2021

(30) Foreign Application Priority Data
Dec. 10, 2019   (KR) .................. 10-2019-0163796

(51) Int. Cl.
*A61N 1/05*     (2006.01)
*A61N 1/36*    (2006.01)
(Continued)

(52) U.S. Cl.
CPC ........... *A61N 1/36002* (2017.08); *A61N 1/05* (2013.01); *A61N 1/3787* (2013.01); *H02N 1/04* (2013.01)

(58) Field of Classification Search
CPC ... H02N 1/04; H02N 1/08; H02N 2/18; A61N 1/3787; A61N 1/05; A61N 1/36002; A61N 1/378; A61N 1/40; A61N 1/362; A61N 1/3605; A61N 2007/0021; A61B 2018/00398; A61B 17/70; A61B 17/7002; A61B 5/0022; A61B 5/0075; A61B 5/01; A61B 5/062; A61B 5/11; A61B 5/4528;
(Continued)

(56) References Cited

U.S. PATENT DOCUMENTS

2017/0187306 A1*   6/2017   Yeo .................. B29C 33/424

* cited by examiner

*Primary Examiner* — Carl H Layno
*Assistant Examiner* — Anh-Khoa N Dinh
(74) *Attorney, Agent, or Firm* — NSIP Law

(57) ABSTRACT

A triboelectric energy generator includes a substrate, a first triboelectric member disposed on the substrate in a first partial region of a top face of the substrate, a second triboelectric member disposed on the substrate in a second partial region of the top of the substrate, a third triboelectric member disposed above and spaced from the first triboelectric member and the second triboelectric member. The first triboelectric member, the second triboelectric member, and the third triboelectric member are made of different materials. When an ultrasonic wave is applied to a top face of the third triboelectric member, the third triboelectric member is constructed to alternately contact and non-contact both the first triboelectric member and the second triboelectric member, thereby to generate triboelectricity.

11 Claims, 5 Drawing Sheets

(51) Int. Cl.
*A61N 1/378* (2006.01)
*H02N 1/04* (2006.01)

(58) Field of Classification Search
CPC ... A61B 5/4571; A61B 5/4576; A61B 5/4585; A61B 5/4851; A61B 5/686; A61B 5/6878; A61B 5/6882; A61B 5/6885; A61B 5/7275; A61B 5/7282; A61B 5/742; A61B 5/746; G03G 9/1075; G03G 9/1135; G03G 9/1136; G03G 15/0812; G03G 2215/0634; G03G 2215/0866; G03G 9/097; G03G 9/09708; G03G 9/09716; G03G 9/108; G03G 9/1087; G03G 9/10884; G03G 9/1131; G03G 9/1137; G03G 9/1138; G03G 9/1139
See application file for complete search history.

METHOD OF INHIBITING PROLIFERATION OF TUMOR CELL USING TRIBOELECTRIC ENERGY GENERATOR USING ULTRASONIC WAVE

CROSS-REFERENCE TO RELATED APPLICATIONS

This application claims the benefit under 35 USC 119(a) of Korean Patent Application No. 10-2019-0163796 filed on Dec. 10, 2019, in the Korean Intellectual Property Office, the entire disclosures of which are incorporated herein by reference for all purposes.

BACKGROUND

1. Field

The present disclosure relates to a triboelectric energy generator using an ultrasonic waves, and further relates to an implantable treatment device for suppressing spread of tumor including the triboelectric energy generator.

2. Description of Related Art

Conventional methods of treating malignant tumor cells, that is, cancer cells, include drug treatment, radiation therapy, and physical removal. However, in such conventional treatments, not only cancer cells but also normal cells may be removed. Thus, serious mental and physical pains occur. Further, fundamental treatment may not be achieved and thus there is a risk of recurrence.

In 2004, a research result was published that spread of only malignant tumors is inhibited using an electric field without chemical treatment or surgery. This electric field based scheme is commercialized. However, in this scheme, a cancer patient has to carry a power supply that is as large as a backpack. This may interfere with daily life. Further, malignant tumor cells in blood vessels or lymph gland may not be treated. Thus, it is important to develop a treatment scheme that may only affect malignant tumor cells, does not have the risk of recurrence, and may minimize mental and physical pains.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure intends to provide a new structure of a triboelectric energy generator using ultrasonic waves.

Further, a purpose of the present disclosure is to provide a treatment device using a triboelectric energy harvester that uses ultrasonic waves that are harmless to the human body and is implantable into a body via minimal surgery, thereby treating even malignant tumor cells circulating in blood vessels and lymph gland with superior malignant tumor spread inhibition and without side effects such as the mental and physical pains and recurrence thereof.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

A first aspect of the present disclosure provides a triboelectric energy generator using ultrasonic wave, the generator comprising: a substrate; a first triboelectric member disposed on the substrate and in a first partial region of an top face of the substrate; a second triboelectric member disposed on the substrate in a second region of the top of the substrate, wherein the second region is different from the first region; and a third triboelectric member disposed above and spaced from the first triboelectric member and the second triboelectric member, wherein the first triboelectric member, the second triboelectric member, and the third triboelectric member are made of different materials, wherein the material of the third triboelectric member has a position between positions of the materials of the first triboelectric member and the second triboelectric member on a triboelectric series, wherein when an ultrasonic wave is applied to a top face of the third triboelectric member, the third triboelectric member is constructed to alternately contact and non-contact both of the first triboelectric member and the second triboelectric member, thereby to generate triboelectricity.

In one implementation of the first aspect, one of the first triboelectric member and the second triboelectric member is made of a material having a positively charged property on the triboelectric series, and the other thereof is made of a material having a negatively charged property on the triboelectric series.

In one implementation of the first aspect, the third triboelectric member is made of a polymer material.

In one implementation of the first aspect, a first electrode is disposed between the first triboelectric member and the substrate, and a second electrode is disposed between the second triboelectric member and the substrate.

In one implementation of the first aspect, the first triboelectric member and the second triboelectric member have the same thickness.

In one implementation of the first aspect, an area of the first partial region is equal to an area of the second partial region.

In one implementation of the first aspect, a first spacer is disposed between the first triboelectric member and the third triboelectric member, and a second spacer is disposed between the second triboelectric member and the third triboelectric member.

In one implementation of the first aspect, the energy generator is packaged.

A second aspect of the present disclosure provides an implantable tumor treatment device comprising: the triboelectric energy generator as defined above; first and second wires respectively connected to the first triboelectric member and the second triboelectric member; and first and second insulated electrodes respectively connected to distal ends of the first and second wires, and facing away each other.

In one implementation of the second aspect, a treatment target tumor cell is sandwiched between the first and second insulated electrodes, wherein an ultrasonic wave is applied from an outside of a body into the triboelectric energy generator embedded in the body to generate electricity to generate an electric field between the first and second insulated electrodes.

In one implementation of the second aspect, the applied ultrasonic wave has a frequency of 10 kHz to 1 MHz.

A third aspect of the present disclosure provides a triboelectric energy generator using ultrasonic wave, the generator comprising: a substrate; a first triboelectric member disposed on the substrate; and a second triboelectric member disposed above and spaced apart from the first triboelectric member, wherein the first triboelectric member and the second triboelectric member are made of different materials, wherein when an ultrasonic wave is applied to a top face of the second triboelectric member, the second triboelectric member is constructed to alternately contact and non-contact the first triboelectric member, thereby to generate triboelectricity.

In one implementation of the third aspect, the second triboelectric member is made of a conductive polymer hydrogel.

In one implementation of the third aspect, a spacer is disposed between the first triboelectric member and the second triboelectric member.

In one implementation of the third aspect, the energy generator is packaged.

In one implementation of the third aspect, an electrode is disposed on the substrate, wherein a first pacer is disposed between the first triboelectric member and the electrode, wherein a second spacer is disposed between the first triboelectric member and the second triboelectric member, wherein when the ultrasonic wave is applied to the second triboelectric member, the second triboelectric member is constructed to alternately contact and non-contact the first triboelectric member, and then, the first triboelectric member is constructed to alternately contact and non-contact the electrode to generate further triboelectricity.

In one implementation of the third aspect, a first electrode is disposed below and spaced apart from the first triboelectric member, wherein a second electrode is disposed below and spaced apart from the second triboelectric member, wherein a polymer material layer is disposed between the second electrode and the first triboelectric member.

A fourth aspect of the present disclosure provides an implantable tumor treatment device comprising: the triboelectric energy generator of the third aspect; first and second wires respectively connected to the first triboelectric member and the second triboelectric member; and first and second insulated electrodes respectively connected to distal ends of the first and second wires, and facing away each other.

In one implementation of the fourth aspect, a treatment target tumor cell is sandwiched between the first and second insulated electrodes, wherein an ultrasonic wave is applied from an outside of a body into the triboelectric energy generator embedded in the body to generate electricity to generate an electric field between the first and second insulated electrodes.

In one implementation of the fourth aspect, the applied ultrasonic wave has a frequency of 10 kHz to 1 MHz.

Effects of the present disclosure may be as follows but may not be limited thereto.

The triboelectric energy generator disclosed in the present disclosure may generate the triboelectric energy using the ultrasonic waves.

Further, according to the present disclosure, the triboelectric energy generator that uses the ultrasonic wave may be implantable into the body. Thus, when the ultrasonic wave is applied thereto, the triboelectric energy generator embedded in the body may generate electrical power. Thus, a separate power source is not required. The device including the generator may treat circulating malignant tumor cells and thus may be expected to have great technical and medical significances.

In addition to the effects as described above, specific effects of the present disclosure will be described together with the detailed description for carrying out the disclosure.

DETAILED DESCRIPTIONS

Figure 1:
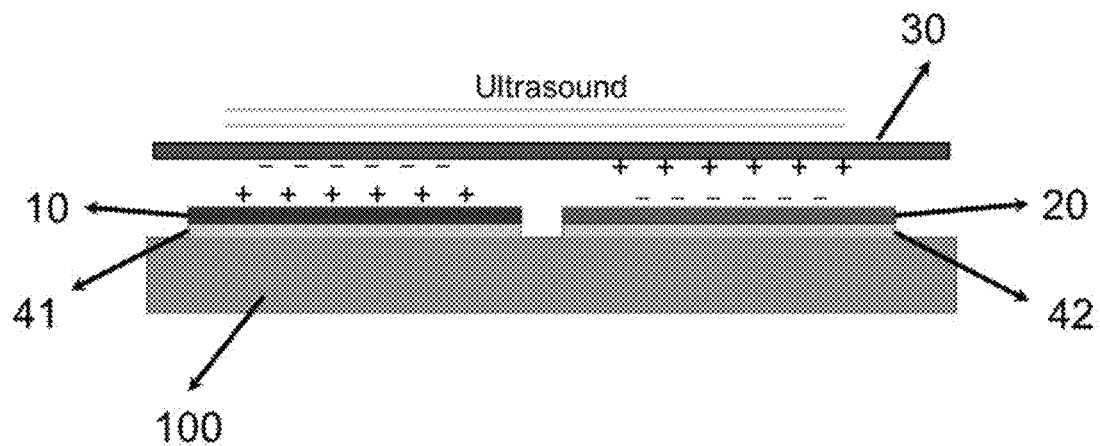
FIG. 1 shows a cross-sectional view of a triboelectric energy generator using an ultrasonic wave according to an embodiment of the present disclosure.

For simplicity and clarity of illustration, elements in the figures are not necessarily drawn to scale. The same reference numbers in different figures denote the same or similar elements, and as such perform similar functionality. Moreover, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure may suggest a technology that suppresses spread of malignant tumors by generating and applying an electric field in a form of alternating currents to the tumor using a triboelectric energy harvester that may generate electric power when applying an ultrasonic wave in a frequency band of 10 kHz to 1 MHz thereto.

The present disclosure may suggest two types of triboelectric energy harvesters using ultrasonic waves that may suppress the spread of the malignant tumors as described above. Configurations of the two types of the harvesters will be described sequentially below.

FIG. 1 shows a cross-sectional view of a triboelectric energy generator using an ultrasonic wave according to an embodiment of the present disclosure.

As shown in FIG. 1, a triboelectric energy generator using an ultrasonic wave according to an embodiment of the present disclosure may include a substrate 100; a first triboelectric member 10; a second triboelectric member 20; and a third triboelectric member 30.

The substrate 100 may be made of any material that may be used for a conventional substrate. The substrate may be made of a polymer that is harmless to a human body, for example, Teflon but is not limited thereto.

The first triboelectric member 10 is disposed on the substrate 100. As shown in FIG. 1, the first triboelectric member 10 is disposed on a first partial region of a top face of the substrate.

The second triboelectric member 20 is disposed on the substrate 100. As shown in FIG. 1, the second triboelectric member 20 is disposed on a second partial region of the top face of the substrate other than the first partial region. In this case, the first triboelectric member 10 and the second triboelectric member 20 are not connected to each other.

The first triboelectric member and the second triboelectric member are made of different materials. In this case, preferably, the first triboelectric member and the second triboelectric member may be made of materials having a large difference between charged properties on a triboelectric series thereof. For example, when the first triboelectric member is made of a material exhibiting a positively charged property, the second triboelectric member may be made of a material exhibiting a negatively charged property. In another example, when the first triboelectric member is made of a material exhibiting a negatively charged property, the second triboelectric member may be made of a material exhibiting a positively charged property.

In this case, each of the first triboelectric member and the second triboelectric member may be made of a material having electrical conductivity. Alternatively, when each of the first triboelectric member and the second triboelectric member may be made of a non-conductive material, first and second electrodes 41 and 42 may be disposed beneath the first triboelectric member and the second triboelectric member, respectively, as shown in FIG. 1.

Further, the first triboelectric member 10 and the second triboelectric member 20 preferably have the same thickness. This is because it is desirable that the third triboelectric member 30 is in concurrent contact with the first triboelectric member 10 and the second triboelectric member 20 via the application of the ultrasonic wave to generate an AC type of current. The same thickness thereof means that vertical dimensions of the first triboelectric member 10 and the second triboelectric member 20 on the substrate are equal to each other.

Further, it is preferable that sizes of the first and second partial regions occupied by the first triboelectric member and the second triboelectric member, respectively is the same. This is because it is desirable that when the third triboelectric member 30 is in concurrent contact with the first triboelectric member 10 and the second triboelectric member 20, a magnitude of the AC type of current may be constant.

The third triboelectric member 30 is upwardly spaced apart from the first triboelectric member and the second triboelectric member. In this connection, the third triboelectric member 30 may be sized such that the third triboelectric member 30 comes into contact with the first triboelectric member 10 and the second triboelectric member 20 simultaneously via the application of the ultrasonic wave.

In one example, the first triboelectric member, the second triboelectric member and the third triboelectric member may be made of different materials. In this case, the third triboelectric member 30 has a position between positions of the first triboelectric member and the second triboelectric member on the triboelectric series. This is because when the third triboelectric member concurrently contacts the first triboelectric member and the second triboelectric member, one of the first triboelectric member and the second triboelectric member is positively charged while the other thereof is negatively charged, thereby to generate a voltage output in a form of alternating current. This AC type output may be identified in an OSC section in FIG. 2.

When the ultrasonic wave is applied to a top face of the third triboelectric member, the third triboelectric member alternately contacts and non-contacts the first triboelectric member and the second triboelectric member, such that triboelectricity is generated, and thus an alternating electric field is generated.

The third triboelectric member may refer to a member to which the ultrasonic wave is applied and may be preferably made of a polymer material. The third triboelectric member may be made of a polymer that does not reflect the ultrasonic waves and may transmit the ultrasonic waves reliably. The third triboelectric member may not include a metal. This is because a significant amount of the ultrasonic wave is reflected from the metal and thus the wave is weakened.

In another example, although not shown, the energy generator according to the present disclosure may be packaged. Typically, the packaging may be achieved using silicon.

Figure 2:
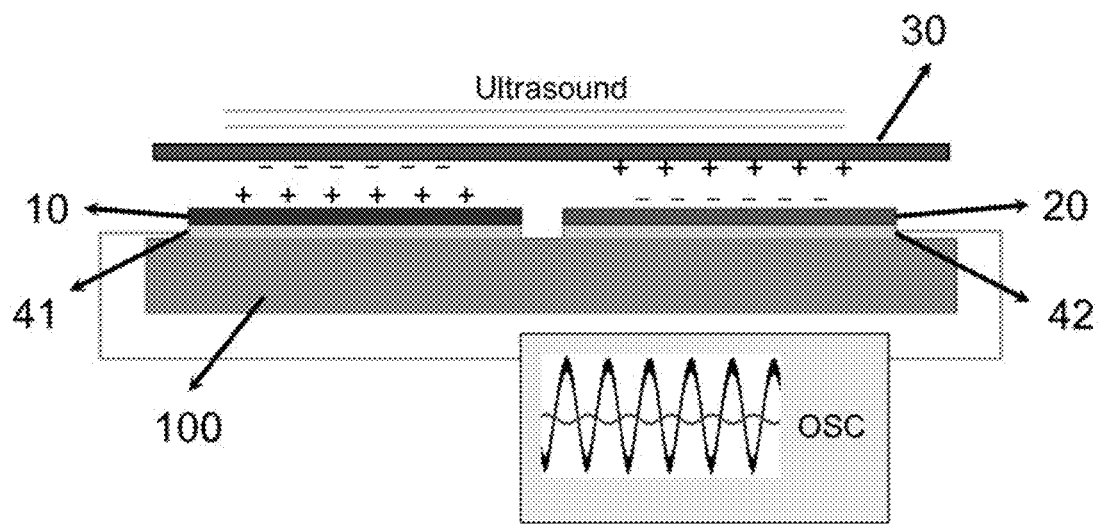
FIG. 2 shows an additional cross-sectional view of a triboelectric energy generator using an ultrasonic wave according to an embodiment of the present disclosure.

FIG. 2 shows an additional cross-sectional view of a triboelectric energy generator using an ultrasonic wave according to an embodiment of the present disclosure.

A triboelectric energy generator using an ultrasonic wave in FIG. 2 further has a spacer 50 and wires which are not shown in the embodiment of FIG. 1.

As shown in FIG. 2, the spacers 50 may be optionally disposed between the first triboelectric member and the third triboelectric member, and between the second triboelectric member and the third triboelectric member.

Figure 3:
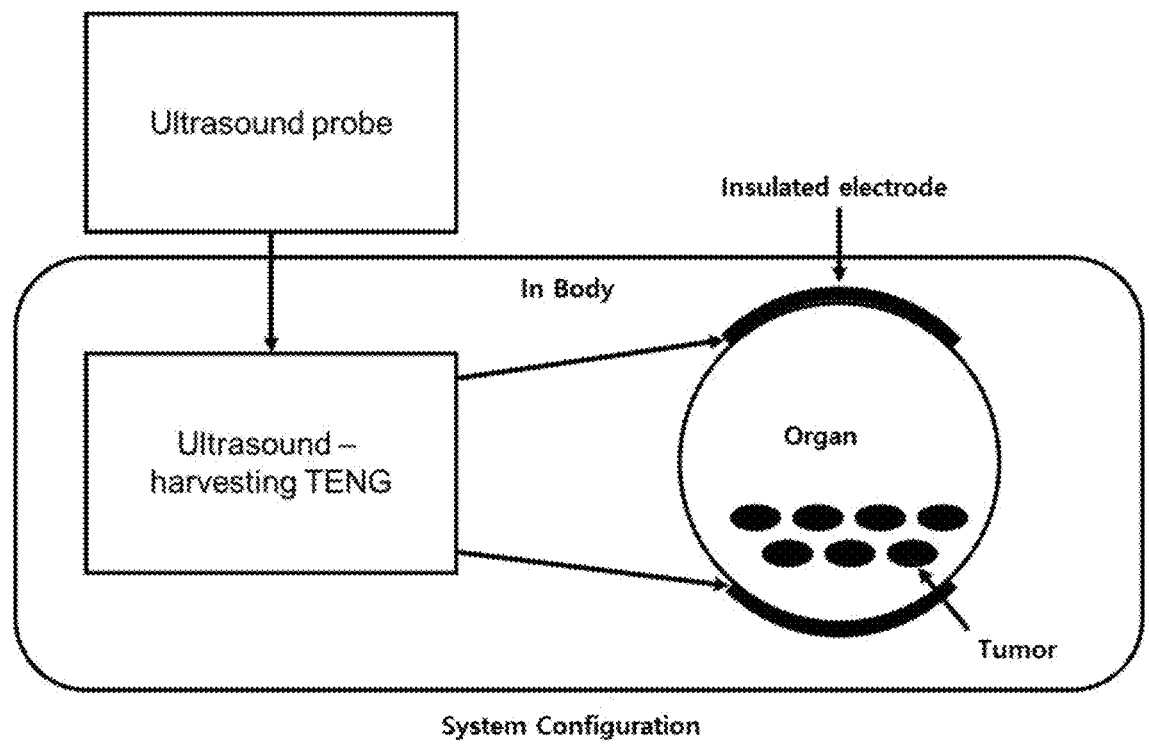
FIG. 3 shows a system configuration diagram of an implantable tumor treatment device according to an embodiment of the present disclosure.
Figure 4:
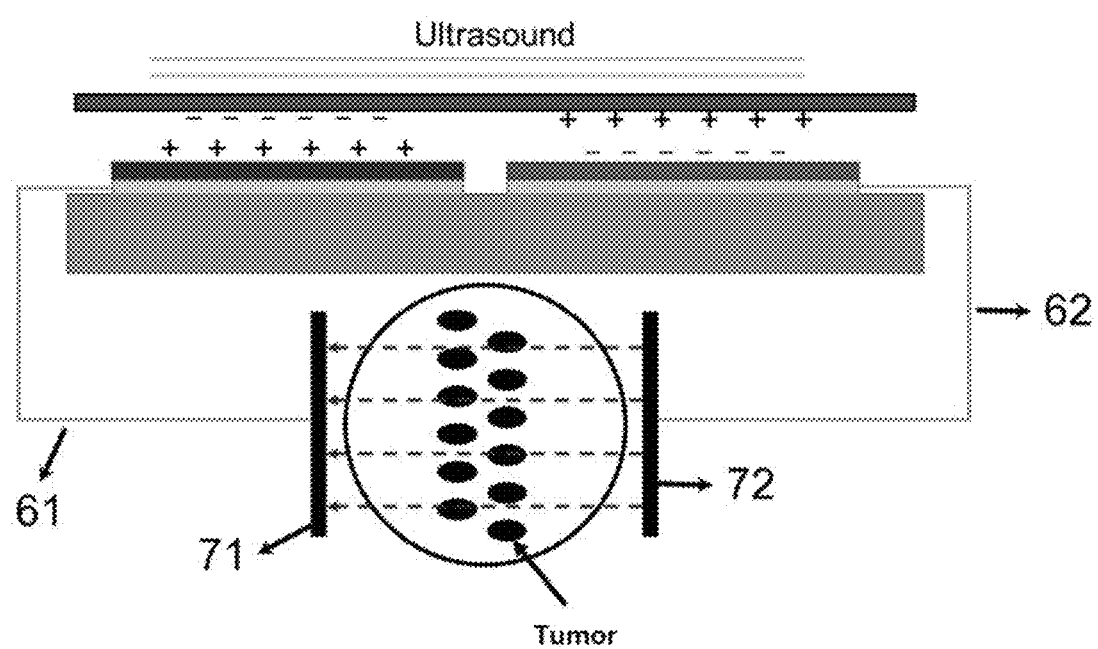
FIG. 4 shows a cross-sectional view of an implantable tumor treatment device according to an embodiment of the present disclosure.

FIG. 3 shows a system configuration diagram of an implantable tumor treatment device according to an embodiment of the present disclosure. FIG. 4 shows a cross-sectional view of an implantable tumor treatment device according to an embodiment of the present disclosure.

The implantable tumor treatment device capable of self-power generation may be implemented using the triboelectric energy generator using an ultrasonic wave according to an embodiment of the present disclosure as described above.

The implantable tumor treatment device according to an embodiment of the present disclosure includes the triboelectric energy generator using an ultrasonic wave, first and second wires 61 and 62 connected to the first triboelectric member and the second triboelectric member as shown in FIG. 2, respectively, and first and second insulated electrodes 71 and 72 connected to distal ends of the first and second wires and facing away each other.

Referring to the system as shown in FIG. 3, the system may be composed of three components: a triboelectric energy generator that uses an implantable ultrasonic wave, an ultrasonic wave probe that generates an ultrasonic wave of a frequency that is effective in suppressing growth of malignant tumors, and tumor contacts electrodes that may be attached to the tumor.

The tumor may be sandwiched between the first and second insulated electrodes. When applying an ultrasonic wave from an outside of the body to the triboelectric energy generator inserted in the body to generate electricity, the alternating electric field may be generated between the first and second insulated electrode, thereby to cure the tumor and inhibit the tumor spread.

It is preferable to use an ultrasonic wave of a frequency range that does not affect normal cells, for example, a frequency range of 10 kHz to 1 MHz. When applying an ultrasonic wave having an intensity that does not harm the human body and the frequency range of 10 kHz to 1 MHz, the spread of malignant tumors may be effectively suppressed with minimal surgery. Thus, it is expected that technical and medical significances of the tumor treatment device according to the present disclosure will be great in that the device may reduce serious mental and physical pains which otherwise occur in the conventional treatment scheme.

In the above descriptions, the first embodiment of the triboelectric energy generator using the ultrasonic wave according to the present disclosure and the implantable tumor treatment device using the same has been described. Hereinafter, a second embodiment of a triboelectric energy generator using an ultrasonic wave according to the present disclosure and an implantable tumor treatment device using the same will be described. Redundant descriptions of the first embodiment as described above will be omitted.

Figure 5:
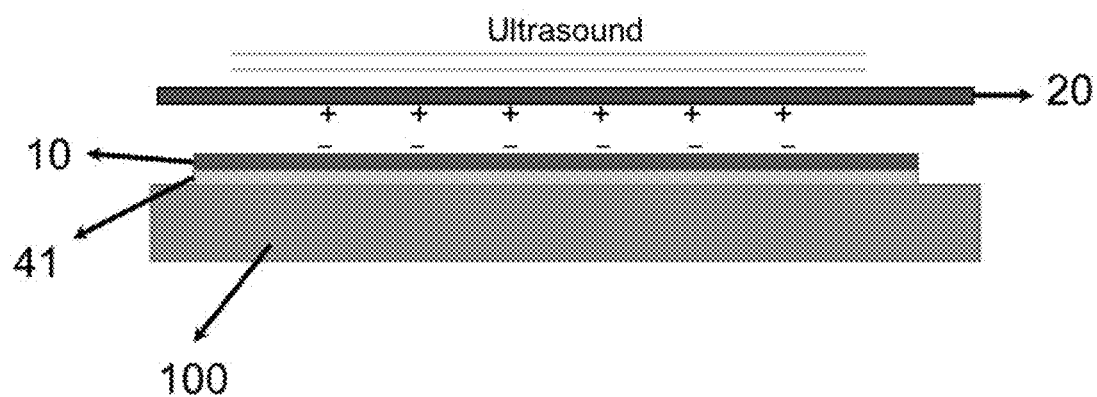
FIG. 5 shows a cross-sectional view of a triboelectric energy generator using an ultrasonic wave according to an additional embodiment of the present disclosure.

FIG. 5 shows a cross-sectional view of a triboelectric energy generator using an ultrasonic wave according to an additional embodiment of the present disclosure.

A triboelectric energy generator using an ultrasonic wave according to an additional embodiment of the present disclosure may include a substrate 100; a first triboelectric member 10; and a second triboelectric member 20.

As shown in FIG. 5, the first triboelectric member 10 is disposed on the substrate 100. The second triboelectric member 20 is upwardly spaced apart from the first triboelectric member and contacts or non-contacts the first triboelectric member via the application of the ultrasonic wave. The first triboelectric member and the second triboelectric member are made of different materials. The first triboelectric member and the second triboelectric member may have a greater difference between charged properties on the triboelectric series thereof.

A separate electrode 41 may be disposed between the substrate and the first triboelectric member as shown in FIG. 5.

The second triboelectric member is preferably made of a conductive polymer hydrogel. The second triboelectric member 20 acts as a triboelectric member and also acts as an electrode. Examples of the hydrogel may include PEDOT:PSS, polyaniline, and polypyrrole.

When an ultrasonic wave is applied to a top face of the second triboelectric member, the second triboelectric member alternately contacts and non-contacts the first triboelectric member, such that triboelectricity is generated.

Figure 6:
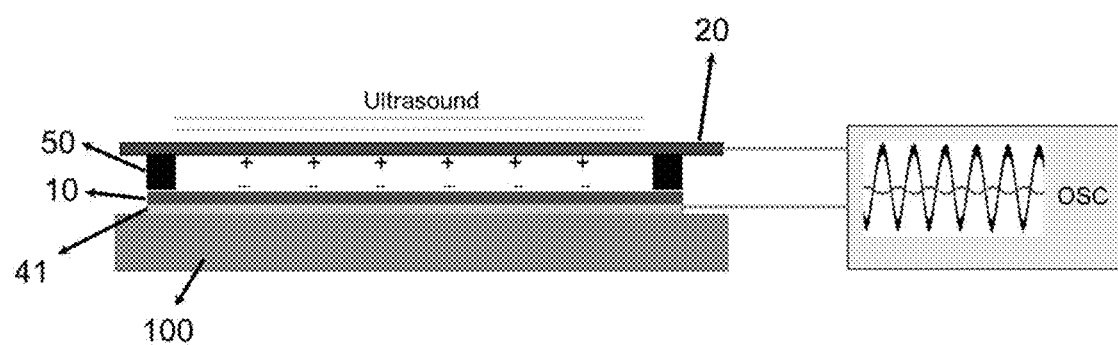
FIG. 6 shows an additional cross-sectional view of a triboelectric energy generator using an ultrasonic wave according to an additional embodiment of the present disclosure.

FIG. 6 shows an additional cross-sectional view of a triboelectric energy generator using an ultrasonic wave according to an additional embodiment of the present disclosure. As shown in FIG. 6, first and second wires are connected to the first triboelectric member and the second triboelectric member, respectively to generate an alternating electric field.

A spacer 50 may be optionally disposed between the first triboelectric member and the second triboelectric member. The energy generator may be optionally packaged.

Figure 8:
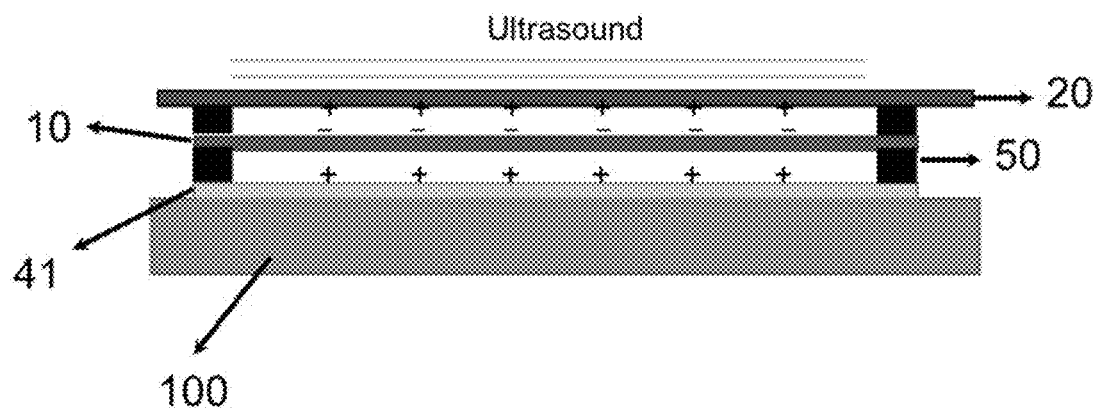
FIG. 8 shows a cross-sectional view of a triboelectric energy generator using an ultrasonic wave according to an additional embodiment of the present disclosure.

FIG. 8 shows that the spacer 50 is disposed between the first triboelectric member 10 and the second triboelectric member 20 and a further spacer is disposed between the electrode 41 and the first triboelectric member 10. In this case, when the ultrasonic wave is applied to the second triboelectric member 20, the first triboelectric member 10 alternately contacts and non-contacts both of the second triboelectric member 20 and the electrode 41 to further increase the triboelectric energy.

Figure 7:
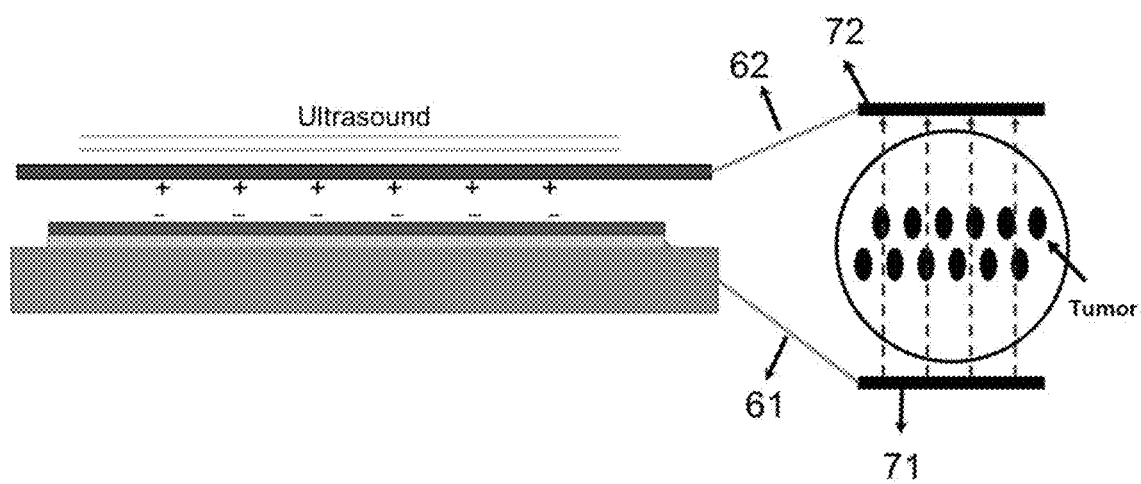
FIG. 7 shows a cross-sectional view of an implantable tumor treatment device according to an additional embodiment of the present disclosure.

FIG. 7 shows a cross-sectional view of an implantable tumor treatment device according to an additional embodiment of the present disclosure.

An implantable tumor treatment device according to an additional embodiment of the present disclosure includes the triboelectric energy generator using an ultrasonic wave, as described above.

The implantable tumor treatment device according to the additional embodiment of the present disclosure includes the triboelectric energy generator using an ultrasonic wave, first and second wires 61 and 62 connected to the first triboelectric member and the second triboelectric member as shown in FIG. 7, respectively, and first and second insulated electrodes 71 and 72 connected to distal ends of the first and second wires and facing away each other.

Referring to the system as shown in FIG. 3, the system may be composed of three components: a triboelectric energy generator that uses an implantable ultrasonic wave, an ultrasonic wave probe that generates an ultrasonic wave of a frequency that is effective in suppressing growth of malignant tumors, and tumor contacts electrodes that may be attached to the tumor.

The tumor may be sandwiched between the first and second insulated electrodes. When applying an ultrasonic wave from an outside of the body to the triboelectric energy generator inserted in the body to generate electricity, the alternating electric field may be generated between the first and second insulated electrode, thereby to cure the tumor and inhibit the tumor spread.

It is preferable to use an ultrasonic wave of a frequency range that does not affect normal cells, for example, a frequency range of 10 kHz to 1 MHz. When applying an ultrasonic wave having an intensity that does not harm the human body and the frequency range of 10 kHz to 1 MHz, the spread of malignant tumors may be effectively suppressed with minimal surgery. Thus, it is expected that technical and medical significances of the tumor treatment device according to the present disclosure will be great in that the device may reduce serious mental and physical pains which otherwise occur in the conventional treatment scheme.

Figure 9:
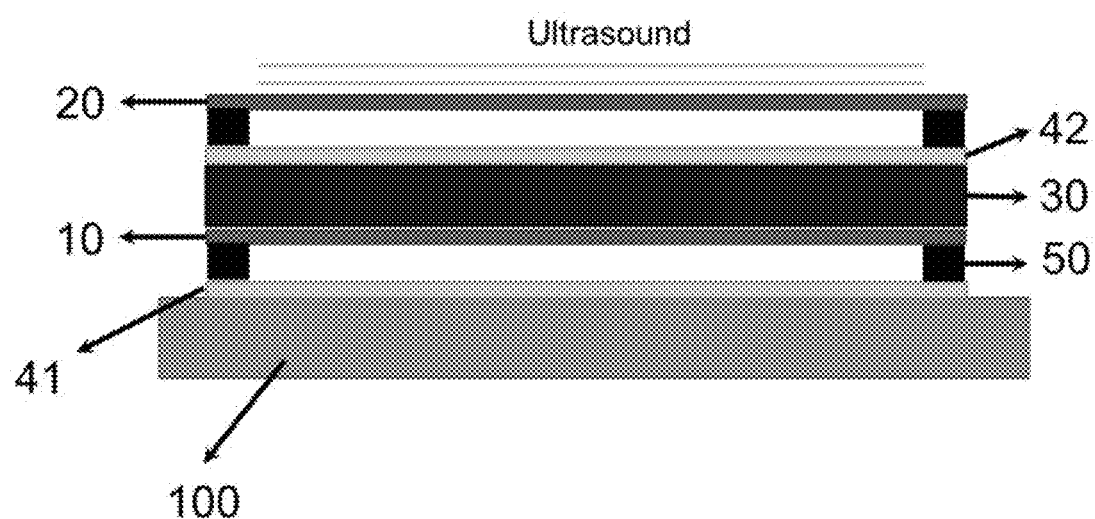
FIG. 9 shows a cross-sectional view of a triboelectric energy generator using an ultrasonic wave according to an additional embodiment of the present disclosure.

FIG. 9 shows a structure of a triboelectric energy generator using an ultrasonic wave according to an additional embodiment of the present disclosure. FIG. 9 is characterized by addition of a polymer material layer 30. The polymer material layer 30 may include PDMS (poly(dimethylsiloxane)), epoxy resin, and polyurethane. In the structure of FIG. 9, when an ultrasonic wave is applied to the second triboelectric member 20, first triboelectric electricity is generated via alternate contact and non-contact between the second triboelectric member 20 and a second electrode layer 42 disposed on the polymer material layer 30 in a upper portion of the device. Then, the ultrasonic wave passes through the polymer material layer 30. Subsequently, the ultrasonic wave reaches a lower portion of the device such that second triboelectric electricity is generated via alternate contact and non-contact between the first triboelectric member 10 and a first electrode layer 41 disposed on the substrate. Thus, as the ultrasonic wave passes through the polymer material layer 30, the first and second triboelectric energy may be generated to maximize the total triboelectric energy.

In another example of FIG. 9, a first spacer 50 may be disposed between the first triboelectric member and the first electrode layer and a second spacer 50 may be disposed between the second triboelectric member and second electrode layer.

Figure 10:
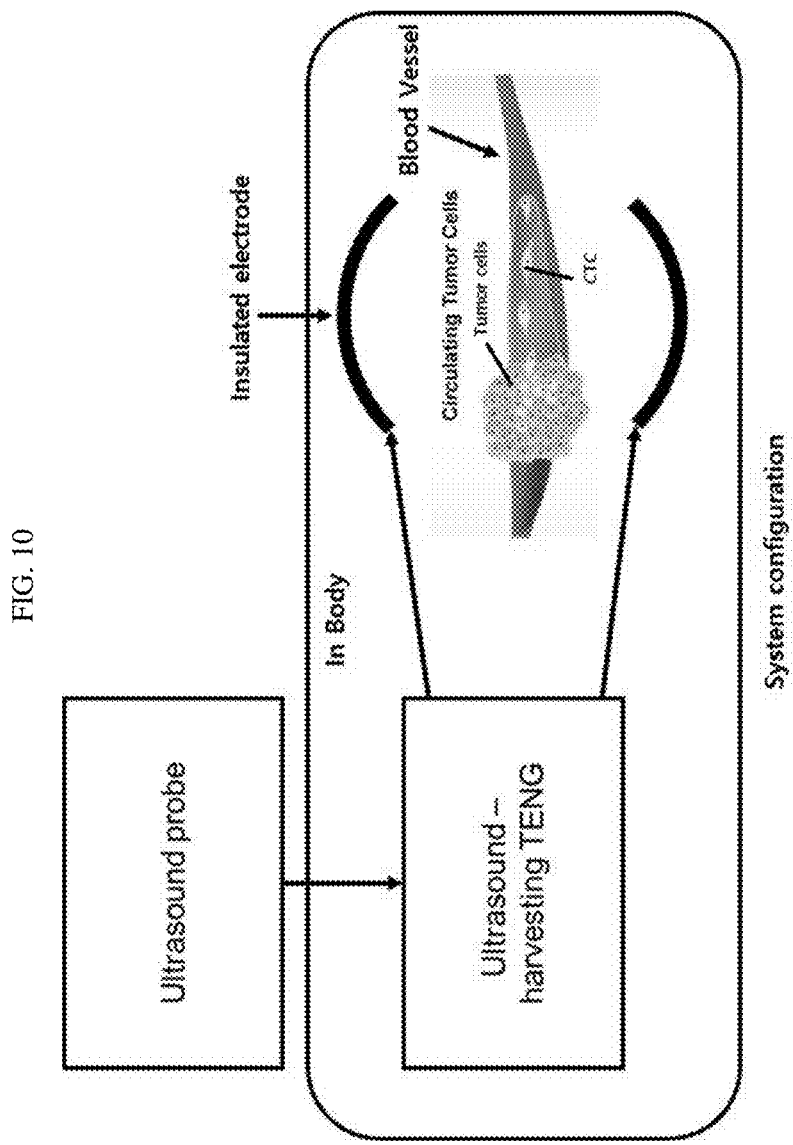
FIG. 10 is a diagram of the system configuration describing an effect of application of an electric field on a tumor.

FIG. 10 is a diagram of a system configuration describing an effect of application of an electric field on the tumor.

As shown in FIG. 10, an electric field may be generated from the first and second insulated electrodes implanted in the body. The spread of malignant tumors may be suppressed with this electric field. Thus, the device according to the present disclosure may be capable of treating even malignant tumors circulating in blood vessels and lymph glands, which may otherwise not be cured with the conventional anticancer treatment methods.

The malignant tumor cells present the in blood vessels or lymph gland may not be specifically targeted and treated in the conventional treatment methods such as drug treatment, radiation therapy, and physical removal. However, according to the present disclosure, the triboelectric energy harvester that may be implanted in the body may be applied to cure the malignant tumor cells present the in blood vessels or lymph gland. Thus, it is expected that the spread of the malignant tumor cells circulating in blood vessels and lymph glands as well as malignant tumors in cellular tissues may be suppressed.

Compared with generation of an electric field using a conventional skin-attached electrode and the malignant tumor spread inhibition using the electric field, the electric field may be applied to a highly localized area due to the implantation of the device according to the present disclosure into the body. In this connection, it is known that the spread inhibition effect increases in proportion to the intensity of the electric field. Thus, according to the present disclosure, the inhibition effect is expected to be superior to that using the skin-attached electrode.

It will be understood that although the above disclosure has been described with reference to the preferred embodiment of the present disclosure, those skilled in the art may achieve modifications and changes thereto within a range that does not deviate from the spirit and region of the present disclosure as described in the following claims.

What is claimed is:

1. A triboelectric energy generator using ultrasonic wave, the generator comprising:
   a substrate;
   a first triboelectric member disposed on the substrate and in a first partial region of a top face of the substrate;

a second triboelectric member disposed on the substrate in a second partial region of the top of the substrate, wherein the second partial region is different from the first partial region; and a third triboelectric member disposed above and spaced from the first triboelectric member and the second triboelectric member, wherein the first triboelectric member, the second triboelectric member, and the third triboelectric member are made of different materials, wherein the material of the third triboelectric member has a position between positions of the materials of the first triboelectric member and the second triboelectric member on a triboelectric series, wherein, when an ultrasonic wave is applied to a top face of the third triboelectric member, the third triboelectric member is constructed to alternately contact and non-contact both of the first triboelectric member and the second triboelectric member, thereby to generate triboelectricity.

2. The triboelectric energy generator of claim 1, wherein one of the first triboelectric member and the second triboelectric member is made of a material having a positively charged property on the triboelectric series, and other among the first triboelectric member and the second triboelectric member is made of a material having a negatively charged property on the triboelectric series.

3. The triboelectric energy generator of claim 1, wherein the third triboelectric member is made of a polymer material.

4. The triboelectric energy generator of claim 1, wherein a first electrode is disposed between the first triboelectric member and the substrate, and a second electrode is disposed between the second triboelectric member and the substrate.

5. The triboelectric energy generator of claim 1, wherein the first triboelectric member and the second triboelectric member have the same thickness.

6. The triboelectric energy generator of claim 1, wherein an area of the first partial region is equal to an area of the second partial region.

7. The triboelectric energy generator of claim 1, wherein a first spacer is disposed between the first triboelectric member and the third triboelectric member, and a second spacer is disposed between the second triboelectric member and the third triboelectric member.

8. The triboelectric energy generator of claim 1, wherein the energy generator is packaged.

9. An implantable tumor treatment device comprising:
the triboelectric energy generator of claim 1;
first and second wires respectively connected to the first triboelectric member and the second triboelectric member; and
first and second insulated electrodes respectively connected to distal ends of the first and second wires, and facing away each other.

10. The device of claim 9, wherein a treatment target tumor cell is sandwiched between the first and second insulated electrodes, wherein an ultrasonic wave is applied from an outside of a body into the triboelectric energy generator embedded in the body to generate electricity to generate an electric field between the first and second insulated electrodes.

11. The device of claim 10, wherein the applied ultrasonic wave has a frequency of 10 kHz to 1 MHz.

* * * * *